United States Patent [19]
Scott et al.

[11] Patent Number: 5,580,894
[45] Date of Patent: Dec. 3, 1996

[54] ISOXAZOLYL ENAMINONES

[75] Inventors: Kenneth R. Scott, Silver Spring; Ivan O. Edafiogho, Oxon Hill, both of Md.; Ralph R. Roberts, Cottage Grove, Minn.

[73] Assignee: Howard University, Washington, D.C.

[21] Appl. No.: 585,329

[22] Filed: Jan. 11, 1996

[51] Int. Cl.$^6$ .......................... A61K 31/41; C07D 261/10
[52] U.S. Cl. .......................... 514/380; 548/243; 548/244; 548/246
[58] Field of Search ........................... 514/380; 548/243, 548/244, 246

[56] References Cited

U.S. PATENT DOCUMENTS 5,468,775  11/1995  Scott et al. ............................. 514/380

FOREIGN PATENT DOCUMENTS

| 2341537 | 8/1973 | Germany. |
| 48-48464 | 7/1973 | Japan. |
| 49-51272 | 4/1974 | Japan. |
| 49-124061 | 11/1974 | Japan. |
| 50-46662 | 4/1975 | Japan. |
| 50-46664 | 4/1975 | Japan. |

OTHER PUBLICATIONS

Edafiogho et al., Synthesis . . . enaminoes., J. Med. Chem. 1992, 35, pp. 2798–2805.
Scott et al., Synthesis . . . enaminones., Further . . . correlations., J. Med. Chem. 1993, 36, pp. 1947–1955.
Molzac et al., The profile . . . rats., Epilepsia, 1993, 1141–1146.
Edafiogho et al., Anticonvulsant . . . (ADD 196022). Curr. Med. Chem., 1994, 1, 161–177.
Edafiogho et al., Nuclear magnetic . . . enaminones. J. Pharm. Sci., 1994, 83, 1155–1170.
Scott et al., Synthesis . . . enaminones. 3. Investigations . . . evaluations., J. Med. Chem., 1995, 38, 4033–4043.
Johnston et al., Central . . . muscimol., Biochem. Pharmacol., 1968, 17, 2488–2489.
Curtis et al., Bicaculline, . . . cat., Brain Res. 1971, 32, 69–96.
Johnston et al., Muscimol . . . brain slices., Psycho pharmacologia, 1971, 22, 230–233.
Schousboe et al., Inhibition . . . compounds., Brain Res., 1978, 153, 623–626.
Krogsgaard–Larsen et al., In Progress in Medicinal Chemistry, vol. 22, 1986, 68–120.
Krogsgaard–Larsen et al., A new class of GABA agonist., Nature (London), 1977, 268, 53–55.
Lin et al., Synthesis . . . activator Abstracts of papers, 208th National Meeting American Chemical Society, 1994.
Spencer et al., Condensation . . . Ketone., J. Org. Chem., 1964, 29, 787–789.
Friary et al., Heterocyclic . . . acids. J. Org. Chem., 1973, 38, 3487–3490.
CA 91: 193411v Isoxazolium salts, Mizugai et al., p. 659, 1979.
Chemical And Pharmacological Properties Of Alkylated 3–Isoxazolidones; S. K. Germane, A. D. Voitenko and Ya. A. Kastron; Institute of Organic Synthesis, Academy of Sciences of the Latvian SSR, Riga. Translated from Khimiko–Farmatsevticheskii Zhurnal, vol. 9, No. 2, pp. 28–30, Feb., 1975.
Comparative pharmacological study of substituted carboxamides upon central nervous system, O. Foussard–Blanpin., Ann. Pharm. Fr., 1982, 40, 339–350.
Chem. Pharm Bull., 34(4), pp. 1643–1655 (1986), Isoxazole Derivatives as Centrally Acting Muscle Relaxants. II., Synthesis and Structure–Activity Relationship of 3–Amino–N–(3–phenyl–5–isoxazolyl)propanamides),
Tochiro Tatee, Kazuhisa Narita, Shuji Kurashige, Shinji Ito, Hiroshi Yamanaka, Michinao Mizugaki, Takao Sakamoto and Hideomi Fukuda.

*Primary Examiner*—Joseph K. McKane
*Attorney, Agent, or Firm*—Kenyon & Kenyon

[57] ABSTRACT

An oxazolyl enaminone is provided having the formula:

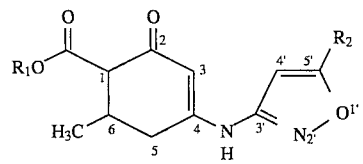

wherein $R_1$ is selected from the group consisting of a branched or unbranched alkyl groups containing from 1 to 4 carbon atoms and $R_2$ is selected from the group consisting of a branched or unbranched alkyl group containing from 1 to 4 carbon atoms, a chloro group, a trifluoromethyl group and a trifluoromethoxy group. Also provided are pharmaceutically acceptable salts and isomers of the above, and pharmaceutical compositions containing the same.

12 Claims, No Drawings

ISOXAZOLYL ENAMINONES

FIELD OF THE INVENTION

This invention relates to novel synthetic organic compounds having significant central nervous system activity. More particularly, this invention relates to novel oxazolyl enaminones and to methods for their synthesis.

BACKGROUND OF THE INVENTION

Enaminones are a class of enamines, i.e., α,β-unsaturated amines analogous to enols. Enamines are Schiff bases, and are highly unstable in aqueous solutions. As such, enamines are used as potential prodrugs (agents which yield an amine on hydrolysis) providing a lipophilic, but acid-labile, carrier group to the active pharmacophore.

Anticonvulsant enaminones have been developed through previous work [1] by Dr. K. R. Scott and others at Howard University. Based on the success of this work the present inventors have synthesized a homologous series of enaminone esters bearing an isoxazole moiety. The isoxazole ring system was found to be a potent and selective GABA receptor agonist in earlier work of Johnston et al., [2] and Curtis et al. [3] on muscimol, 5. Johnston [4] later found muscimol to possess weak, but specific, GABA uptake inhibitory properties on rat brain slices, while Schosboe et al. [5] found the same property in cultured astrocytes. The anticonvulsant effect of muscimol [6] and the GABA$_A$ receptor agonist THIP (4,5,6,7-tetrahydro-isoxazolo[5,4-c]pyridin-3-ol), 6 [7] both of which exert their specific action on postsynaptic GABA receptors, is also known.

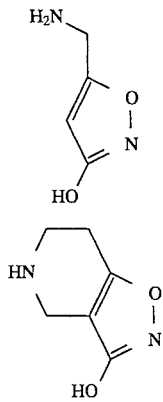

The substitution of the methyl group on the isoxazole ring was also reported as producing a highly potent cholinergic channel activator, 7 [8].

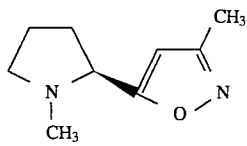

SUMMARY OF THE INVENTION

According to one embodiment of the invention, an oxazolyl enaminone is provided having the formula:

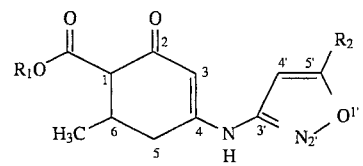

wherein $R_1$ is selected from the group consisting of a branched or unbranched alkyl groups containing from 1 to 4 carbon atoms and $R_2$ is selected from the group consisting of a branched or unbranched alkyl group containing from 1 to 4 carbon atoms, a chloro group, a trifluoromethyl group and a trifluoromethoxy group. Also provided are pharmaceutically acceptable salts and isomers of the above.

According to another embodiment of the present invention, a pharmaceutical composition is provided comprising an effective amount of the above oxazolyl enaminone and a pharmaceutically acceptable carrier.

According to yet another embodiment of the present invention, a method of treating grand mal and partial seizures in a mammal is provided comprising administering to the mammal an effective amount of the above oxazolyl enaminone.

The compounds of the present invention are extremely potent in causing various biological responses. For that reason, these compounds are useful for pharmacological purposes.

The above oxazolyl enaminones are advantageous in that they are central nervous system agents having anticonvulsive activity, with particularly exceptional potency against electroshock seizures.

Due to the biological response to these compounds, the compounds of the present invention are useful to prevent, alleviate, control or study a variety of diseases and undesirable psychological conditions in mammals, including humans, pets, zoological specimens, domestic animals, and laboratory animals, such as monkeys, rabbits, rats and mice. Such diseases and conditions include epilepsy, parkinsonism, Huntington's chorea and Alzheimers disease.

These compounds are also advantageous in that they demonstrate little or no neurotoxicity at dosages up to 100 mg/kg and above.

These and other embodiments and the advantages will become readily apparent upon reading the description, examples and claims to follow. Unless indicated to the contrary, all references cited herein are incorporated by reference in their entireties.

DETAILED DESCRIPTION

Synthesis

Isoxazole enaminones are synthesized according to the following scheme. Isoxazoles are condensed with the respective β-hydroxy keto esters, 1a–c, as previously reported [1a, 1b, 1f,9]. Prerequisite β-hydroxy keto esters, 1a–c, are synthesized via a condensation of ethyl crotonate with the respective acetoacetic esters as reported by Friary and coworkers for the synthesis of the 4-carbo-tert-butoxy-5-methylcyclohexane-1,3-dione, 1c [10], and recently reported by Scott et al. [1f]. The subsequent condensation reaction of the β-hydroxy keto esters, 1a–c, with 3-amino-5-methyl-isoxazole, 2, proceeds smoothly to provide easily recrystallizable products, 3 a–c.

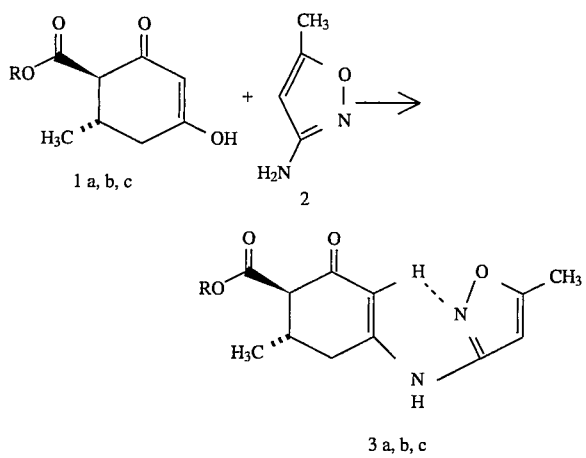

Where a, R=tert-Bu; b, R=Et; c, R=Me

The starting isoxazole, 2, employed in the current study has a hetero ring like that of muscimol, 5. However, it should be noted that in the current series, a lipophilic methyl group replaces the highly ionic and hydrophilic 2-moiety, while an amino group replaces the hydroxyl moiety.

The compounds of the present invention can be readily provided in the form of pharmaceutically acceptable salts. Suitable pharmaceutically acceptable salts include salts derived from inorganic or organic acids. Typical examples of pharmaceutically acceptable salts include salts derived from inorganic acids such as hydrochloric acid, hydrobromic acid, sulfuric acid, phosphoric acid, nitric acid and the like, and organic acids such as acetic acid, propionic acid, glycolic acid, oxalic acid, pyruvic acid, malic acid, succinic acid, malonic acid, maleic acid, fumaric acid, citric acid, tartaric acid, mandelic acid, cinnamic acid, benzoic acid, p-toluenesulfonic acid, salicylic acid, ethane sulfonic acid, methanesulfonic acid and so forth. The formation of such salts is well within the abilities of those of ordinary skill in the art.

ADMINISTRATION

For each utility and indication, the amount of ingredient required will depend upon a number of factors including the severity of the condition to be treated and the identity of the recipient, and will ultimately be at the discretion of the attendant physician or veterinarian. In general however, for each of these utilities and indications, a suitable effective dose will preferably be in the range 0.1 to 250 mg per kilogram bodyweight of recipient per day, more preferably in the range 0.1 to 10 mg per kilogram bodyweight per day.

While it is possible for the active ingredients to be administered alone it is preferable to present them as pharmaceutical formulations. The formulations, both for veterinary and for human use, of the present invention comprise at least one active ingredient, as defined above, together with one or more acceptable carriers thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include a step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into tablet form, for example.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as a bolus, electuary or paste.

A tablet may be made by compression or molding, optionally with one or more pharmaceutically acceptable excipients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredient therein.

For topical applications, the formulations are preferably applied as an ointment or cream. When formulated in an ointment, the active ingredients may be employed with either a paraffinic or water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

Formulations suitable for topical administration to the eye also include eye drops wherein the active ingredient is dissolved (or suspended) in a suitable carrier, especially in aqueous solvent for the active ingredient.

Formulations suitable for topical administration in the mouth include lozenges containing the active ingredient, preferably in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a stearate.

Formulations suitable for nasal administration wherein the carrier is a solid include a coarse powder having a particle size, for example, in the range of from about 20 to about 500 microns, which is administered by rapid inhalation through the nasal passage. Suitable formulations wherein the carrier is a liquid, for administration as, for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injection, immediately prior to use. Extemporaneous injection solutions and suspensions may be prepared from sterile powders, granules and tablets of the kind previously described. Formulations for intramuscular administration are particularly preferred.

Preferred unit dosage formulations are those containing a daily dose or daily sub-dose, as herein above recited, or an appropriate fraction thereof, of an active ingredient.

It should be understood that, in addition to the ingredients particularly mentioned above, the formulations of this invention may include other agents conventional in the art having regard to the type of formulation in question. For example, those suitable for oral administration may include flavoring agents.

The present invention further provides veterinary compositions containing at least one active ingredient as above defined together with a veterinary carrier thereof.

Veterinary carriers are materials useful for the purpose of administering the composition and may be solid, liquid or gaseous materials useful for the purpose of administering the composition and are otherwise inert or acceptable in the veterinary art and are compatible with the active ingredient. These veterinary compositions may be administered orally, parenterally or by any other desired route.

For oral administration, the compositions can be in the form of a tablet, granule drench, paste, cachet, capsule or feed supplement. Granules may be made by the well known techniques of wet granulation, precompression or slugging. They can be administered to animals via an inert liquid vehicle so as to form a drench, or in a suspension with water or oil base. Preferably, further accessory ingredients, such as a dispensing agent, are included.

Additional formulation information can be found, for example, in U.S. Pat. No. 5,079,252.

NMR Analysis

Cyclic enaminone esters of the isoxazole series are shown in Table I. High field ($^1$H and $^{13}$C) Nuclear Magnetic Resonance (NMR) analyses on the reported compounds were consistent with the assigned structures. The $^1$H NMR studies on these compounds proved interesting and unique and differed significantly in the vinyl proton signal from methyl 4-[(p-chlorophenyl)amino]-6-methyl-2-oxocyclohex-3-en-1-oate, (ADD 196022) [1c, 1d], 4 (Table II), the prototypic anticonvulsant in the series. Whereas the vinyl proton of 4 occurred at δ5.48 ppm, the isoxazolyl enaminones herein reported occurred between about δ 6.01–6.02 for the $C_3$ and about δ6.23–6.25 ppm for the $C_4$ isoxazolyl protons, respectively. The unequivocal assignment of these protons was provided by 1D NOE analysis of 3b. On irradiating the $C_5$ methyl on the isoxazole ring, only the $C_4$, proton should show a NOE, which in fact occurred. The 1D NOE spectrum showed a methyl singlet at about δ2.25 ppm and a respective proton NOE at about δ6.02 ppm. In compound 8, methyl 4'-[(4'-chloro-2'-pyridinyl)amino]-6-methyl-2-oxocyclohex-3-en-1-oate [1b, 1d], the vinyl proton appeared at δ6.82 ppm and indicated a deshielding effect, indicative of hydrogen bonding. This was further supported by the acidic NH proton of 8 (δ9.57 ppm, saturated solution), being more deshielded than 4 (δ7.96 ppm, saturated solution) [1a].

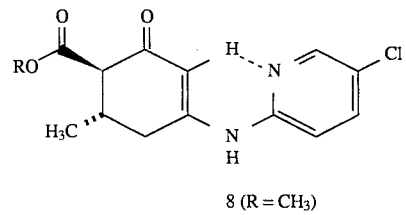

8 (R = CH$_3$)

TABLE I $^{13}$C Correlation chart for compounds 3 and 4.

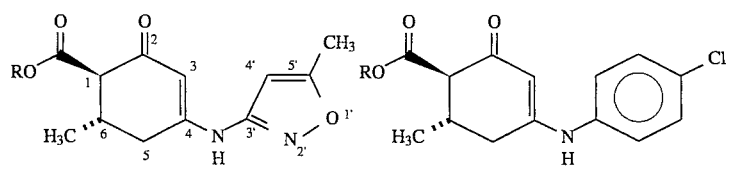

3: a, R = tert-Bu
b, R = Et
c, R = Me

4: R = Me

|  |  | 3a | 3b | 3c | 4 |
|---|---|---|---|---|---|
| Isoxazole (C$_4$) | CH$_3$ | 11.83 | 11.73 | 11.78 | — |
| Me(C$_6$) | CH$_3$ | 19.11 | 19.07 | 19.20 | 19.27 |
| C$_6$ | CH | 31.82 | 31.62 | 31.64 | 31.65 |
| C$_5$ | CH$_2$ | 34.71 | 34.60 | 34.60 | 35.07 |
| C$_1$ | CH | 60.66 | 59.74 | 59.74 | 60.00 |
|  | CH | 95.80 | 95.71 | 95.77 | 96.79(94.64) |
|  | CH | 104.25 | 103.98 | 103.95 |  |
|  | C | 157.15 | 157.31 | 157.45 |  |

TABLE I-continued

¹³C Correlation chart for compounds 3 and 4.

3: a, R = tert-Bu
   b, R = Et
   c, R = Me

4: R = Me

|  |  | 3a | 3b | 3c | 4 |
|---|---|---|---|---|---|
|  | C | 159.54 | 159.42 | 159.47* | 161.33 |
|  | C | 168.75 | 168.67 | 168.78 |  |
| Ketone($C_2$) | C | 169.77 | 170.39 | 170.97 | 171.16 |
| Ester | C=O | 193.13 | 192.70 | 192.70 | 191.11 |
|  | R−O−C=O | 27.77(q), 80.02(s) | 14.04(q), 59.90(t) | 51.43 | 51.35 |
|  |  |  |  |  | 124.64(d) |
|  |  |  |  |  | 128.46(q) |
|  |  |  |  |  | 129.14(d) |
|  |  |  |  |  | 137.65(q) |

TABLE II

¹H Correlation chart for compounds 3c and 4.

| Compound | a | b | c | d | e | f | g |
|---|---|---|---|---|---|---|---|
| 4 | 1.08 (d, 3H) | 2.22–2.98 (m, 3H) 3.08 (d, J=11.00 Hz) | 3.75 (s, 3H) | 5.48 (s, 1H) | 6.86 (bs, 1H) | 7.20–7.50 (m, 5H) | — |
| 3c | 0.98 (d, 3H) | 2.38–2.48 (m, 3H) 3.14 (d, 1H) | 3.64 (s, 1H) | 6.02 (s, 1H) | 9.64 (bs, 1H) | 6.24 (s, 1H) | 2.36 (s, 3H) |

Pharmacology

Preliminary pharmacological testing of the compounds listed in Table I have been provided using procedures that have been described [11]. There are three initial tests: maximal electroshock seizure (MES); subcutaneous pentylenetetrazol (scMet); and neurologic toxicity (Tox) in mice. Intraperitoneal administration of the test compounds was as a suspension in 0.5% methylcellulose. These phase I data are shown in Table III. As previously reported [1b], due to species specificity, all class 1 and 2 active enaminone analogs (activity at 100 mg/kg or less and activity at doses greater than 100 mg/kg but less than 300 mg/kg, respectively), are subsequently evaluated for oral (po) activity (phases VIA and VIB) in the rat, which has been previously shown to be more sensitive to these compounds. As noted from Table III, each of the compounds is a class 1 analog, all displaying activity in the MES intraperitoneal evaluation at 100 mg/kg at 30 min, and 3c is also active at that dose in the 4 h evaluation. The most potent analog, however, is 3b, which is active in the MES evaluation at 30 mg/kg. 3c is also active in the scMet evaluation at 30 mg/kg, at 30 min, however at 300 mg/kg, the animal exhibits continuous seizure activity. It should be noted that 3c is the only compound shown to cause motor impairment at 300 mg/kg, either at 30 min or 4 h, while none of these compounds exhibits toxicity at the lower dosages. Thus, compounds 3b and 3c were further evaluated in a phase VIA study to ascertain their po activity in rats. Table IV details this analysis and reveals that these compounds are also active in rats at 30 mg/kg while displaying minimal motor impairment over the 4 h evaluation. Compound 3b, due to its greater overall potency in both phase I and phase VIA evaluations, was further evaluated in phase VIB to quantitate its activity and toxicity.

Additionally, a special Phase II intraperitoneal rat evaluation of each of these analogs was performed. This data is shown in Table V and compared to compound 4, which was previously reported [1b]. The MES evaluations, at 10 mg/kg were followed at 15, and 30 min, and at 1, 2, 4 and 6 h, while the toxicity evaluations, at 100 mg/kg (except for 3a, which was evaluated at 56 mg/kg), were observed at the six time periods previously indicated and, in addition, at 8 and at 24 h. Compound 3b displays activity at 15 min, and at 1 h, while 3c also shows activity at 15 min, as well as at 1 and 2 h. Compound 3a shows no protection at 10 mg/kg. The toxicity evaluation indicates that none of the isoxazoles exhibits motor impairment throughout the test period. Further, none of the animals exhibits toxicity after 24 h.

TABLE V

Phase II intraperitoneal Rat Toxicity data of Compounds 3a, 3b, 3c and 4.

| Time (h) | MES 10 mg/kg | | | | Tox 100 mg/kg | | | |
|---|---|---|---|---|---|---|---|---|
| | 3a | 3b | 3c | 4 | 3a[c] | 3b | 3c | 4 |
| 0.25 | 0/4 | 3/4 | 1/4 | nd[d] | 0/8 | 0/8 | 0/8 | 0/8 |
| 0.50 | 0/4 | 0/4 | 0/4 | nd[d] | 0/8 | 0/8 | 0/8 | 3/8 |
| 1.00 | 0/4 | 0/4 | 1/4 | nd[d] | 0/8 | 0/8 | 0/8 | 6/8 |
| 2.00 | 0/4 | 0/4 | 1/4 | nd[d] | 0/8 | 0/8 | 0/8 | 7/8 |
| 4.00 | 0/4 | 0/4 | 0/4 | nd[d] | 0/8 | 0/8 | 0/8 | 4/8 |
| 6.00 | 0/4 | 0/4 | 0/4 | nd[d] | 0/8 | 0/8 | 0/8 | 1/8 |
| 8.00 | nd[d] | nd[d] | nd[d] | nd[d] | 0/8 | 0/8 | 0/8 | 0/8 |
| 24.00 | nd[d] | nd[d] | nd[d] | nd[d] | 0/8 | 0/8 | 0/8 | 2/8[e] |

[c]Rotorod toxicity taken at 56 mg/kg.
[d]nd = not determined.
[e]Two animals died.

EXAMPLES:

Materials and Methods

Melting points were determined on a Thomas-Hoover capillary melting point apparatus and are uncorrected. IR spectra were recorded on samples in Nujol, as diluted chloroform solutions in matched sodium chloride cells, or neat with a Perkin-Elmer 1330 spectrophotometer. $^1$H NMR

TABLE III

| | | Anticonvulsant Screening Project (ASP) - Phase I Test Results | | | | | | |
|---|---|---|---|---|---|---|---|---|
| Compound | Dose, mg/kg | scMet,[a] 30 min | scMet,[a] 4 h | MES,[b] 30 min | MES,[b] 4 h | Tox,[c] 30 min | Tox,[c] 4 h | ASP classification[d] |
| 3a | 100 | 0/1 | 0/1 | 2/3 | 0/3 | 0/8 | 0/4 | 1 |
| | 300 | 0/1 | 0/1 | 1/1 | 1/1 | 0/4 | 0/2 | |
| 3b | 30 | 0/1 | 0/1 | 1/1 | 0/1 | 0/4 | 0/2 | 1 |
| | 100 | 0/1 | 0/1 | 2/3 | 0/3 | 0/8 | 0/4 | |
| | 300 | 0/1 | 0/1 | 1/1 | 0/1 | 0/4 | 0/2 | |
| 3c | 30 | 1/5 | 0/1 | 0/1 | 0/1 | 0/4 | 0/2 | 1 |
| | 100 | 0/1 | 0/1 | 1/3 | 1/6 | 0/8 | 0/4 | |
| | 300 | 0/1[e] | 0/1 | 1/1 | 0/4 | 1/4 | 0/2 | |

[a]Subcutaneous pentylenetetrazol test (number of animals protected/number of animals tested).
[b]Maximal electroshock test (number of animals protected/number of animals tested).
[c]Rotorod toxicity (number of animals exhibiting toxicity/number of animals tested).
[d]Classifications are: 1-anticonvulsant activity at 100 mg/kg or less; 2-anticonvulsant activity at doses greater than 100 mg/kg; 3-no anticonvulsant activity at doses up to and including 300 mg/kg.
[e]Continuous seizure activity.

TABLE IV

Phase VIA Oral Rat data for Compounds 3b and 3c.

| Compound | Dose, mg/kg | Time, h | MES | Tox |
|---|---|---|---|---|
| 3b | 30 | 0.25 | 1/4 | 0/4 |
| | | 0.50 | 2/4 | 0/4 |
| | | 1.00 | 2/4 | 0/4 |
| | | 2.00 | 1/4 | 0/4 |
| | | 4.00 | 4/4 | 0/4 |
| 3c | 30 | 0.25 | 2/4 | 0/4 |
| | | 0.50 | 2/4 | 0/4 |
| | | 1.00 | 1/4 | 0/4 |
| | | 2.00 | 3/4 | 0/4 |
| | | 4.00 | 1/4 | 0/4 | spectra were recorded on a General Electric QE 300-MHz spectrometer in deuterated solvents using tetramethylsilane as an internal reference. $^{13}$C NMR spectra were recorded from the DMSO-d$_6$ (septet at $\delta 39.50 \pm 0.02$ ppm) on the same instrument in the broadband decoupled mode. Signal multiplicities were separately determined by standard distortionless enhancement by polarization transfer (DEPT) [12,13] experiments. Coupling patterns are described as follows: s, singlet; bs, broad singlet; d, doublet; t, triplet; q, quartet; m, multiplet; and 1H, 2H, 3H, etc. as the number of hydrogens integrated within a given coupling pattern. The chemical shifts and the coupling constants were rounded off to one decimal place. TLC analysis employed a n-BuOH-HOAc-H$_2$O (5:4:1) or (5:1:4, upper layer) elution solvent mixture and 5×10-cm or 5×20-cm fluorescent plates (Whatman silica gel 60A). Elemental analyses (C, H, and N) were performed by Schwarzkopf Microanalytical Laboratory, Woodside, N.Y. Where analyses are indicated only by the symbols of the elements, analytical results were within 0.4% of the theoretical values. 4-Carbo-tert-butoxy-5-methylcyclohexane-1,3-dione, 1a [10], 4-carbo-ethoxy-5-methylcyclohexane-1,3-dione, 1b [9], and 4-carbomethoxy-5-methylcyclohexane-1,3-dione, 1c [1a], were prepared by literature methods as indicated. 3-Amino-5-methyl isoxazole, 2, was obtained from Fluka Chemika AG (Germany) and used without further purification.

Preparation of Compound 3a

A mixture of 4-carbo-tert-butoxy-5-methylcyclohexane-1,3-dione, 1a, (6.11 g, 27 mmole, mp 145°–146° C.) (lit. 130°–131.5° C. 10, C,H) and 3-amino-5-methylisoxazole, 2, (3.24 g, 33 mmole) were added to a mixture of absolute EtOH (100 mL) and EtOAc (100 mL) and the solution refluxed and stirred for 6 h. Evaporation under reduced pressure yielded a yellow solid which was recrystallized three times from EtOAc to yield 3.57 g (43%) of tert-butyl 4-[(5'-methyl)-3'-isoxazolylamino]-6-methyl-2-oxocyclohex-3-en-1-oate, 3a, white crystals; mp 197°–201 ° C. (with effervescence) (C,H,N); $^1$H NMR (DMSO-$d_6$): $\delta$1.00 (d, 3H, J=6.0 Hz), 1.42 (s, 9H), 2.35 (s, 3H), 2.44 (m, 2H), 2.51 (m, 1H), 2.93 (d, 1H, J=11.5 Hz), 6.01 (s, 1H), 6.23 (s, 1H), 9.58 (bs, 1H); $^{13}$C (DMSO-$d_6$): $\delta$11.83 (q), 19.11 (q), 27.77 (q), 31.82 (d), 34.71 (t), 60.66 (d), 80.02 (s), 95.80 (d), 104.25 (d), 157.11 (s), 159.54 (s), 168.75 (s), 169.77 (s), 193.13 (s).

Preparation of Compound 3b

In a procedure like that for 3a, ethyl 4-[(5'-methyl)-3'-isoxazolylamino]-6-methyl-2-oxocyclohex-3-en-1-oate, 3b, was produced from 1b and 2 after three recrystallizations from EtOH: yield 5.68 g (76%) of white crystals; mp 195°–197° C. (C,H, N); $^1$H NMR (DMSO-$d_6$): $\delta$1.00 (d, 3H, J=5.7 Hz), 1.20 (t, 3H, J=7.1 Hz), 2.35 (s, 3H), 2.38–2.55 (m, 3H), 3.09 (d, 1H, J=11. Hz), 4.12 (q, 2H, J=7.1 Hz), 6.02 (s, 1H), 6.25 (s, 1H), 9.63 (bs, 1H); $^{13}$C NMR (DMSO-$d_6$): $\delta$11.73 (q), 14.04 (q), 19.07 (q), 31.62 (d), 34.60 (t), 59.74 (d), 59.90 (t), 95.71 (d), 103.98 (d), 157.31 (s), 159.42 (s), 168.67 (s), 170.39 (s), 192.70 (s).

Preparation of Compound 3c 1c and 2 were used to produce methyl 4-[(5'-methyl)-3'-isoxazolylamino]-6-methyl-2-oxocyclohex-3-en-1-oate 3c in a procedure like that for 3a: yield 4.31 g (58%) of white crystals; mp 220°–222° C. (C,H,N); $^1$H NMR (DMSO $d_6$): $\delta$0.98 (d, 3H, J=5.9 Hz), 2.36 (s, 3H), 2.38–2.48 (m, 3H), 3.14 (d, 1H, J=11.6 Hz), 3.64 (s, 3H), 6.02 (s, 1H), 6.24 (s, 1H), 9.64 (bs, 1H); $^{13}$C NMR (DMSO-$d_6$): $\delta$11.78 (q), 19.20 (q), 31.64 (d), 34.64 (t), 51.43 (q), 59.74 (d), 95.77 (d), 103.95 (d), 157.45 (s), 159.47 (s), 168.78 (s), 170.97 (s), 192.70 (s).

Pharmacology Evaluations

Initial evaluations for anticonvulsant activity included phases I, II, VIA and VIB test procedures which have been described [11]. These tests were performed either in male Carworth Farms no. 1 (CF1) mice or male Sprague-Dawley rats. Phase I, a qualitative anticonvulsant intraperitoneal evaluation in mice included three tests: maximal electroshock (MES), subcutaneous (scMet), and the rotorod test for neurological toxicity (Tox).

In the MES test, maximal electroshock seizures are elicited with a 60-cycle alternating current of 50 mA intensity (5–7 times that necessary to elicit minimal electroshock seizures) delivered via corneal electrodes for 0.2 seconds. A drop of 0.9% saline is placed on the eye prior to application of the electrodes in order to prevent the death of the animal. Abolition of the hind limb tonic extension component of the seizure is defined as protection and results are expressed as the number of animals protected/the number of animals tested.

In the sc MET test, eighty-five mg/kg of pentylenetetrazol, which induces seizures in more than 95% of mice, is administered as a 0.5% solution subcutaneously in the posterior midline. The animal is observed for 30 minutes. Failure to observe even a threshold seizure (a single episode of clonic spasms of at least 5 seconds duration) is defined as protection and the results are expressed as the number of animals protected/the number of animals tested.

The rotorod test is used to evaluate neurotoxicity. The animal is placed on a 1 inch diameter knurled plastic rod rotating at 6 rpm. Normal mice can remain on a rod rotating at this speed indefinitely. Neurologic toxicity is defined as the failure of the animal to remain on the rod for 1 minute and the results are expressed as the number of animals protected/the number of animals tested.

Compounds were suspended in 0.5% aqueous methylcellulose and were administered at three dosage levels (30, 100, and 300 mg/kg) with anticonvulsant activity and motor impairment noted 30 min and 4 h after administration. These Phase I data are shown in Table III. Phase VIA was a similar qualitative evaluation to the phase I evaluation, however the test drug was administered orally in rats utilizing the three tests noted previously. These data are shown in Table IV. The phase II test quantitated the anticonvulsant activity and motor impairment observed for the most promising compounds in phase I and phase VIA respectively. Phase II quantified data in CF1 mice by intraperitoneal administration. A special intraperitoneal test in rats was performed at 10 mg/kg for activity and at 100 mg/kg for toxicity. Data on these results is shown in Table V above.

Bibliography 1. (a) Edafiogho, I. O.; Hinko, C. N.; Chang, H.; Moore, J. A.; Mulzac, D.; Nicholson, J. M.; Scott, K. R. Synthesis and anticonvulsant activity of enaminones. *J. Med. Chem.* 1992, 35, 2798–2805. (b) Scott, K. R.; Edafiogho, I. O.; Richardson, E. L.; Farrar, V. A.; Moore, J. A.; Tietz, E. I.; Hinko, C. N.; Chang, H.; El-Assadi, A.; Nicholson, J. M. Synthesis and anticonvulsant activity of enaminones. 2. Further structure activity correlations. *J. Med. Chem.* 1993, 36, 1947–1955. (c) Mulzac, D.; Scott, K. R. The profile of anticonvulsant activity and minimal toxicity of methyl 4-[(p-chlorophenyl)amino]-6-methyl-2-oxocyclohex-3-en-1-oate and some prototype antiepileptic drugs in mice and rats. *Epilepsia* 1993, 1141–1146. (d) Edafiogho, I. O.; Alexander, M. S.; Moore, J. A.; Farrar, V. A.; Scott, K. R. Anticonvulsant enaminones: With emphasis on methyl 4-[(p-chlorophenyl)amino]-6-methyl-2-oxocyclohex-3-en-1-oate (ADD 196022). *Curr. Med. Chem.* 1994, 1, 161–177. (e) Edafiogho, I. O.; Moore, J. A.; Alexander, M. S.; Scott, K. R. Nuclear magnetic resonance studies of anticonvulsant enaminones. *J. Pharm. Sci.* 1994, 83, 1155–1170. (f) Scott, K. R.; Rankin, G. O.; Stables, J. M.; Alexander, M. S.; Edafiogho, I. O.; Farrar, V. A.; Kolen, K. R.; Moore, J. A.; Sims, L. D.; Tonnu, A. D. Synthesis and anticonvulsant activity of enaminones. 3. Investigations on 4'-, 3'-, 2'-, and polysubstituted anilino compounds, sodium channel binding studies, and toxicity evaluations. *J. Med Chem.* 1995, 38, 4033–4043.

2. Johnston, G. A. R.; Curtis, D. R.; de Groat, W. C.; Duggan, A. W. Central actions of ibotenic acid and muscimol. *Biochem. Pharmacol.* 1968, 17, 2488–2489.

3. Curtis, D. R.; Duggan, A. W.; Felix, D.; Johnston, G. A. R. Bicuculline, an antagonist of GABA and synaptic inhibition in the spinal cord of the cat. *Brain Res.* 1971, 32, 69–96.

4. Johnston, G. A. R. Muscimol and the uptake of γ-aminobutyric acid by rat brain slices. *Psychopharmacologia* 1971, 22, 230–233.

5. Schousboe, A.; Krogsgaard-Larsen, P.; Svenneby, G.; Hertz, L. Inhibition of the high-affinity, net uptake of GABA into cultured astrocytes by β-proline, nipecotic acid and other compounds. *Brain Res.* 1978, 153, 623–626.

6. Krogsgaard-Larsen, P.; Falch, E.; Hjeds, H. In *Progress in Medicinal Chemistry*, Vol. 22; Ellis, G. P.; West, G. B., Eds. 1986; Elsevier, Amsterdam, Holland; pp 68–120.

7. Krogsgaard-Larsen, P.; Johnston, G. A. R.; Lodge, D.; Curtis, D. R. A new class of GABA agonist. *Nature* (London), 1977, 268, 53–55.

8. Lin, N.-H.; He, Y.; Anderson, D. J.; Wasicak, J. T.; Kasson, R.; Sweeny, D.; Sullivan, J. P. Synthesis and structure-activity relationships of pyrrolidine-modified analogs of ABT-418, a potent cholinergic channel activator. *Abstracts of Papers*, 208$^{th}$ National Meeting American Chemical Society: Washington, D.C., Aug. 21–25, 1994; Abstr. MEDI 199.

9. Spencer, T. A.; Newton, M. D.; Baldwin, S. W. Condensation of diethyl malonate with methyl vinyl ketone. *J. Org. Chem.* 1964, 29, 787–789.

10. Friary, R. J.; Gilligan, J. M.; Szajewski, R. P.; Falci, K. J.; Franck, R. W. Heterocyclic syntheses via the intramolecular acylation of enamines derived from amino acids. *J. Org. Chem.* 1973, 38, 3487–3490.

11. (a) Anticonvulsant Screening Project, Antiepileptic Drug Development Program, National Institutes of Health, DHEW Publ (NIH) (U.S.) 1978, NIH 78–1093. (b) Porter, R. J.; Cereghino, J. J.; Gladding, G. D.; Hessie, B. J.; Kupferberg, H. J.; Scoville, B.; White, B. G. Antiepileptic drug development program. *Cleveland Clin. Q.* 1984, 51, 293–305. (c) Krall, R. L.; Penry, J. K.; White, B. G.; Kupferberg, H. J.; Swinyard, E. A. Antiepileptic drug development: II. Anticonvulsant drug screening. *Epilepsia* 1978, 19, 400–428.

12. Doddrell, D. M.; Pegg, D. T.; Bendall, M. R. Distortionless enhancement of NMR signals by polarization transfer. *J. Magn. Reson.* 1982, 48, 323–327.

13. Pegg, D. T.; Doddrell, D. M.; Bendall, M. R. Correspondence between INEPT and DEPT pulse sequences for coupled spin-half nuclei. *J. Magn. Reson.* 1983, 51, 264–269.

We claim:

1. An oxazolyl enaminone of the formula:

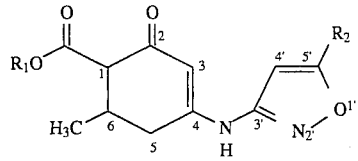

and pharmaceutically acceptable salts thereof, wherein $R_1$ is selected from the group consisting of a branched or unbranched alkyl groups containing from 1 to 4 carbon atoms and $R_2$ is selected from the group consisting of a branched or unbranched alkyl group containing from 1 to 4 carbon atoms, a chloro group, a trifluoromethyl group and a trifluoromethoxy group.

2. The oxazolyl enaminone of claim 1 wherein $R_1$ is a branched or unbranched alkyl group containing from 1 to 4 carbons and $R_2$ is a methyl, ethyl or propyl group.

3. The oxazolyl enaminone of claim 1 wherein $R_1$ is a methyl group and $R_2$ is a methyl group.

4. The oxazolyl enaminone of claim 1 wherein $R_1$ is an ethyl group $R_2$ is a methyl group.

5. The oxazolyl enaminone of claim 1 wherein $R_1$ is a tert-butyl group and $R_2$ is a methyl group.

6. The oxazolyl enaminone of claim 1 having the formula:

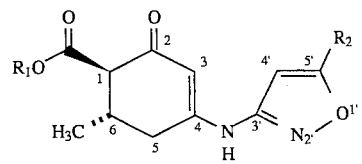

7. The oxazolyl enaminone of claim 6 wherein $R_1$ is a branched or unbranched alkyl group containing from 1 to 4 carbons and $R_2$ is a methyl, ethyl or propyl group.

8. The oxazolyl enaminone of claim 6 wherein $R_1$ is a methyl group and $R_2$ is a methyl group.

9. The oxazolyl enaminone of claim 6 wherein $R_1$ is an ethyl group $R_2$ is a methyl group.

10. The oxazolyl enaminone of claim 6 wherein $R_1$ is a tert-butyl group and $R_2$ is a methyl group.

11. A pharmaceutical composition comprising an effective amount of the oxazolyl enaminone of claim 1 and a pharmaceutically acceptable carrier.

12. A method of treating grand mal and partial seizures in a mammal comprising administering to said mammal an effective amount of an oxazolyl enaminone of claim 1.

* * * * *

UNITED STATES PATENT AND TRADEMARK OFFICE
CERTIFICATE OF CORRECTION

PATENT NO. : 5,580,894
DATED : December 3, 1996
INVENTOR(S) : Kenneth R. Scott, et al.

It is certified that error appears in the above-indentified patent and that said Letters Patent is hereby corrected as shown below:

Column    Line

10    Table V, line 16: Change "2/8ᶜ" to --2/8ᵉ--.

10    19    Change "ᶜTwo animals died." to --ᵉTwo animals died.--.

Signed and Sealed this

Thirteenth Day of May, 1997

Attest:

Attesting Officer

BRUCE LEHMAN

Commissioner of Patents and Trademarks